(12) United States Patent
Coppeta et al.

(10) Patent No.: US 7,114,312 B2
(45) Date of Patent: Oct. 3, 2006

(54) LOW TEMPERATURE METHODS FOR HERMETICALLY SEALING RESERVOIR DEVICES

(75) Inventors: Jonathan R. Coppeta, Windham, NH (US); Scott A. Uhland, Roslindale, MA (US); Benjamin F. Polito, Flagstaff, AZ (US); Norman F. Sheppard, Jr., Bedford, MA (US); Christina M. Feakes, Brighton, MA (US); Douglas B. Snell, Amesbury, MA (US); John T. Santini, Jr., North Chelmsford, MA (US)

(73) Assignee: MicroCHIPS, Inc., Bedford, MA (US)

( * ) Notice: Subject to any disclaimer, the term of this patent is extended or adjusted under 35 U.S.C. 154(b) by 10 days.

(21) Appl. No.: 10/894,265

(22) Filed: Jul. 19, 2004

(65) Prior Publication Data

US 2005/0050859 A1    Mar. 10, 2005

Related U.S. Application Data

(60) Provisional application No. 60/488,123, filed on Jul. 17, 2003.

(51) Int. Cl.
*B65B 7/28* (2006.01)

(52) U.S. Cl. .......................................... 53/471; 53/485

(58) Field of Classification Search .................. None
See application file for complete search history.

(56) References Cited

U.S. PATENT DOCUMENTS

| | | | |
|---|---|---|---|
| 3,564,805 A * | 2/1971 | Mumford | 53/471 |
| 3,932,227 A | 1/1976 | Rothenberg | |
| 4,375,127 A * | 3/1983 | Elkins et al. | 29/623.5 |
| 5,477,009 A * | 12/1995 | Brendecke et al. | 174/52.3 |
| 5,797,898 A | 8/1998 | Santini, Jr. et al. | |
| 6,114,658 A | 9/2000 | Roth et al. | |
| 6,123,861 A | 9/2000 | Santini, Jr. et al. | |
| 6,194,789 B1 | 2/2001 | Zhou | |
| 6,221,024 B1 | 4/2001 | Miesel | |
| 6,232,150 B1 | 5/2001 | Lin et al. | |
| 6,237,398 B1 | 5/2001 | Porat et al. | |
| 6,249,329 B1 * | 6/2001 | Dabral et al. | 349/73 |
| 6,474,879 B1 | 11/2002 | Warnes et al. | |
| 6,491,666 B1 | 12/2002 | Santini, Jr. et al. | |
| 6,527,762 B1 | 3/2003 | Santini, Jr. et al. | |

(Continued)

FOREIGN PATENT DOCUMENTS

JP          63317471 A  * 12/1988
WO    WO 03/068625 A1  *  8/2003

OTHER PUBLICATIONS http:/www.qlpkg.com/product.html (Nov. 15, 2004).

*Primary Examiner*—Stephen F. Gerrity
(74) *Attorney, Agent, or Firm*—Sutherland Asbill & Brennan LLP

(57) ABSTRACT

Methods are provided for hermetically sealing an opening in a reservoir of a containment device. The method comprises applying a polymeric material to an opening in a reservoir of a containment device, the reservoir comprising reservoir contents (such as a drug or a sensor) to be hermetically isolated within the reservoir, the applied polymeric material closing off the opening and forming a temporary seal; and adhering a hermetic sealing material onto the polymeric material to hermetically seal the opening. The reservoir can be a micro-reservoir. The containment device can comprises an array of two or more of reservoirs, and the method comprises hermetically sealing each of the two or more reservoirs.

43 Claims, 4 Drawing Sheets

U.S. PATENT DOCUMENTS

| | | |
|---|---|---|
| 6,551,838 B1 | 4/2003 | Santini, Jr. et al. |
| 2002/0072784 A1 | 6/2002 | Sheppard, Jr. et al. |
| 2002/0099359 A1 | 7/2002 | Santini, Jr. et al. |
| 2002/0107470 A1 | 8/2002 | Richards et al. |
| 2002/0111601 A1 | 8/2002 | Thompson |
| 2002/0138067 A1 | 9/2002 | Sheppard, Jr. et al. |
| 2002/0151776 A1 | 10/2002 | Shawgo et al. |
| 2002/0183721 A1 | 12/2002 | Santini, Jr. et al. |
| 2002/0187260 A1 | 12/2002 | Sheppard, Jr. et al. |
| 2003/0010808 A1 | 1/2003 | Uhland et al. |
| 2003/0080085 A1 | 5/2003 | Greenberg et al. |
| 2003/0100865 A1 | 5/2003 | Santini, Jr. et al. |
| 2004/0073137 A1 | 4/2004 | Lloyd et al. |
| 2004/0082937 A1 | 4/2004 | Ausiello et al. |
| 2004/0106914 A1 | 6/2004 | Coppeta et al. |
| 2004/0106953 A1 | 6/2004 | Yomtov et al. |
| 2004/0121486 A1 | 6/2004 | Uhland et al. |
| 2004/0127942 A1 | 7/2004 | Yomtov et al. |
| 2004/0166140 A1 | 8/2004 | Santini, Jr. et al. |

* cited by examiner

LOW TEMPERATURE METHODS FOR HERMETICALLY SEALING RESERVOIR DEVICES

CROSS-REFERENCE TO RELATED APPLICATIONS

Benefit of U.S. Provisional Application No. 60/488,123, filed Jul. 17, 2003, is claimed. The application is incorporated herein by reference.

BACKGROUND OF THE INVENTION

This invention is generally in the field of methods and structures for hermetically sealing small reservoirs or apertures in devices.

U.S. Pat. No. 5,797,898, No. 6,527,762, No. 6,491,666, and No. 6,551,838 describe devices for the controlled release or exposure of reservoir contents. The devices include a plurality of reservoirs in which the reservoir contents are contained. For example, the reservoirs could contain drug molecules for release or sensors for exposure. In certain embodiments, these reservoirs have openings that must be sealed to isolate the reservoir contents in each reservoir, to prevent leakage of material from or between any of the reservoirs. In many embodiments, hermeticity is desirable, for example to protect the purity or quality of the reservoir contents. Indeed, for most long-term in vivo applications wherein the microchip device serves as, or is included as part of, an implantable medical device, hermeticity is necessary.

U.S. Pat. No. 6,194,789 discloses a method of hermetic sealing in which an electronic or optoelectronic component is encapsulated in an adhesive and then coated with one or several metallic layers using physical vapor deposition or electroplating. It also discloses interposing multiple layers of adhesives with metallic layers to provide hermeticity and protection for the metallic layers. However, the reference neither relates to MEMS devices and hermetic micro-reservoirs nor addresses issues of biocompatibility, device interaction with drug or patient, and control of polymer deposition.

U.S. Pat. No. 3,932,227 discloses a hermetic seal formed by plating or using a physical vapor deposition technique to deposit a metal onto two inorganic substrates with a narrow gap. The gap is bridged by the deposited metal forming a hermetically sealed assembly. U.S. Pat. No. 6,474,879 discloses the same concept as specifically applied to hermetically sealing a fiber optic cable into ferrule. Again, these references do not address or relate to hermetic sealing of micro-reservoirs, biocompatibility, or device interaction with drug or patient.

U.S. Patent Application Publication 2003/0010808 describes various techniques for hermetically sealing micro-reservoirs. These techniques include high temperature laser or resistive welding, soldering, ultrasonic welding, and metal compression gaskets.

It would be desirable to provide additional or improved methods of hermetically sealing a microchip device or other reservoir devices, particularly for reservoirs containing materials sensitive to elevated temperatures.

SUMMARY OF THE INVENTION

In one aspect, methods are provided for hermetically sealing an opening in a reservoir of a containment device. The method comprises applying a polymeric material to an opening in a reservoir of a containment device, the reservoir comprising reservoir contents to be hermetically isolated within the reservoir, the applied polymeric material closing off the opening and forming a temporary seal; and adhering a hermetic sealing material onto the polymeric material to hermetically seal the opening. In a preferred embodiment, the reservoir is a micro-reservoir. In a preferred embodiment, the containment device comprises an array of two or more micro-reservoirs, and the method comprises sealing the two or more micro-reservoirs.

In one embodiment, the reservoir is closed, at an end distal the opening in need of sealing, by a reservoir cap which can later be selectively disintegrated or permeabilized to expose or release the reservoir contents. In preferred embodiments, the reservoir contents comprise a drug, a sensor, or a combination thereof. For example, the containment device can be part of an implantable drug delivery or sensing device.

The polymeric material can be applied in a number of ways, depending for example on the type or form of the polymeric material. In one embodiment, the polymeric material comprises a thermoplastic. For example, the thermoplastic can be applied to the opening in a molten state and then cooled to solidify and form the temporary seal. In another embodiment, the polymeric material comprises a polyester-based liquid crystal polymer material. In yet another embodiment, the polymeric material comprises a filler material to modify the hermeticity and coefficient of thermal expansion characteristics of the temporary seal. In yet another embodiment, the polymeric material comprises a desiccant.

In a further embodiment, the polymeric material comprises a thermoset. For example, the thermoset can be applied to the opening in a liquid state and then cured to solidify and form the temporary seal. In one embodiment, the thermoset is cured by heating. The heat optionally can be applied to the thermoset in a pulsed manner. In one embodiment, the containment device or a portion thereof is cooled while the thermoset is being heated. In another embodiment, the thermoset is cured by light activation. In still another embodiment, the thermoset cures at ambient temperature after two or more hours. In one method, the thermoset is applied such that the reservoir is underfilled.

In a further embodiment, the polymeric material is applied to the opening in solution with a volatile solvent and then the volatile solvent is evaporated to solidify the polymeric material and form the temporary seal. In another embodiment, the polymeric material comprises a photodefinable polymer.

In another embodiment, the method may further include interposing a barrier layer between the reservoir contents and the polymeric material. In one embodiment, a barrier layer precursor material is dispensed into the reservoir and then is reacted to form the barrier layer. For example, the barrier layer can be selected from among synthetic polymers, sol gel glasses or ceramics, and biopolymers. In one embodiment, the synthetic polymer comprises an epoxy, a silicone, or a polyurethane. In another embodiment, the barrier layer comprises a silica sol gel or a titania sol gel. In yet another embodiment, the barrier layer comprises an alginate, albumin, glutaraldehyde, or combinations thereof.

In a further embodiment, the method further includes placing a solid secondary component into the opening before or after the polymeric material is applied to the opening but before the hermetic sealing material is adhered.

In preferred embodiments, the reservoir is defined in a substrate which has a sealing surface circumscribing the opening of the reservoir. Preferably, the hermetic sealing material is further adhered to the sealing surface at least in an area circumscribing the opening, and preferably, the substrate is formed of one or more hermetic materials. In one embodiment, the sealing surface comprises one or more structures confining the location of the applied polymer. In one embodiment, the one or more structures comprise a trench surrounding the reservoir.

In various embodiments, the hermetic sealing material is selected from the group consisting of titanium, platinum, gold, stainless steels, aluminum, and combinations thereof. In other embodiments, the hermetic sealing material is selected from the group consisting of tin, gold-tin, indium, indium-tin, gold-silicon, polysilicon, and combinations thereof. In still other embodiments, the hermetic sealing material is selected from the group consisting of silicon dioxide, silicon nitride, titanium nitride, and combinations thereof.

In one embodiment, the hermetic sealing material comprises a liquid crystal polymer.

In another aspect, a method is provided for hermetically sealing a plurality of openings of reservoirs in a containment device comprising: providing a device which comprises a substrate in which a plurality of reservoirs are defined, the substrate having a sealing surface circumscribing the openings of the reservoirs; applying a polymeric material to the openings to close off the opening and form a temporary seal; and adhering a hermetic sealing material onto the polymeric material and onto the sealing surface to hermetically seal the opening. In a preferred embodiment, the reservoirs are micro-reservoirs.

In one embodiment, the method further includes, before applying the polymeric material, loading the reservoirs with reservoir contents, which are selected from the group consisting of drugs, sensors, and combinations thereof, wherein the method hermetically isolates the reservoir contents within the reservoir.

One or more polymer pathways may be formed between the two or more reservoirs by the application of the polymeric material. These polymer pathways are removed before the hermetic sealing material is adhered over the temporary seals. In one embodiment, the polymer pathways are removed by dry etching, polishing, or laser ablation.

In another embodiment, a wetting control means is used to manipulate surface tension effects to limit the wetting of the polymer to specific locations on the surface of the substrate. For example, the wetting control means can include depositing and patterning a wetting control agent on the surface of the substrate before application of the polymeric material.

In another aspect, a containment device is provided which has at least one reservoir hermetically sealed by the methods described herein.

BRIEF DESCRIPTION OF THE DRAWINGS

FIG. 5A is a cross-sectional view of a device, FIG. 5B is a close-up of a portion of FIG. 5A, and FIG. 5C is a plan view of a portion of the device in FIG. 5A.

DESCRIPTION OF THE INVENTION

Sealing methods have been developed for use where a low temperature hermetic seal is desirable. They is particularly suitable or adapted for use in making implantable medical devices having reservoirs containing reservoir contents that are sensitive to both heat and mass transport of external molecular species (e.g., a protein drug, a chemical reagent, or a sensing device). With the hermetic sealing methods described herein, heat sensitive materials advantageously incur a minimum thermal load during the process. While primarily developed for use with micro-reservoirs, the methods can be readily adapted for use with macro-reservoirs. Generally, the present hermetic sealing methods involve creating a temporary seal (e.g., by employing a polymer, alone or in combination with another material) to seal the reservoir opening, and then by coating this temporary seal to create the hermetic seal. As used herein, the "temporary seal" is "temporary" only in the sense that it serves as a structure upon which the "permanent" or "true" sealing material, i.e., the hermetic sealing material, can be formed.

As used herein, the term "hermetic" refers to preventing undesirable chemical ingress or egress into or from one or more reservoirs or other compartments of the device over the useful life of the device, using a seal composed of materials, such as ceramics, glasses, and metals, that are essentially impermeable to chemicals and biological fluids, including water, air, and carbon dioxide.

As used herein, the terms "comprise," "comprising," "include," and "including" are intended to be open, non-limiting terms, unless the contrary is expressly indicated.

The Hermetic Sealing Methods and Hermetically Sealed Structures

Methods are provided for hermetically sealing an opening in a reservoir of a containment device. The method comprises applying a polymeric material to an opening in a reservoir of a containment device, the reservoir comprising reservoir contents to be hermetically isolated within the reservoir, the applied polymeric material closing off the opening and forming a temporary seal; and adhering a hermetic sealing material onto the polymeric material to hermetically seal the opening. In a preferred embodiment, the containment device comprises an array of two or more micro-reservoirs, and the method comprises sealing the two or more micro-reservoirs, effectively creating an array of micro-hermetic chambers.

The hermetic sealing methods can be understood with reference to the non-limiting embodiments illustrated in the Figures.

Figure 1:
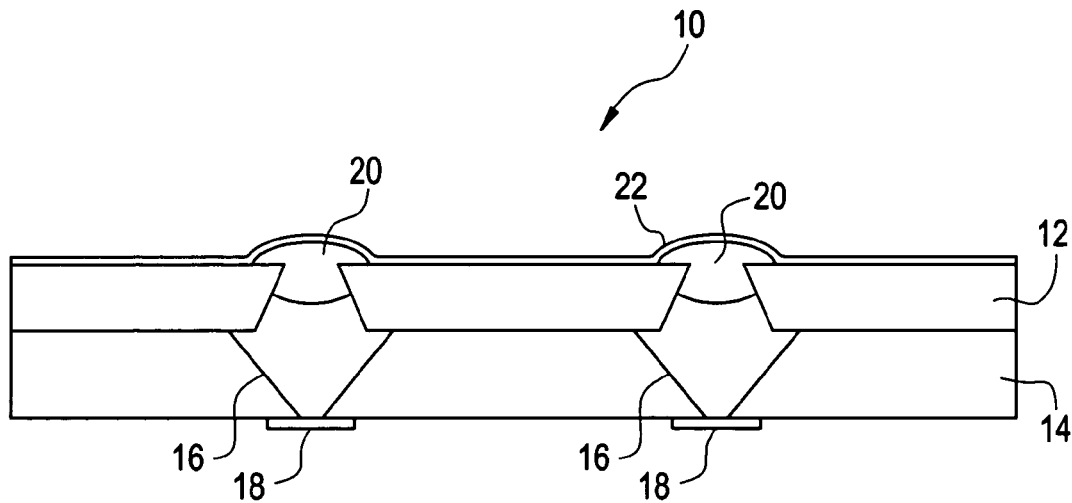
FIG. 1 is a cross-sectional view of a portion of one embodiment of a reservoir device sealed as described herein.

FIG. 1 shows the relevant portion of micro-reservoir device 10. The device includes substrate portions 12 and 14, and an array of reservoirs 16 covered by reservoir caps 18. Each reservoir cap 18 serves as a hermetic seal at one end of each reservoir 16. After loading the reservoirs 16 with reservoir content (not shown), a biocompatible thermoset or thermoplastic polymer 20 is deposited at each reservoir opening at the external surface of substrate portion 12, effectively plugging the opening. Then, a hermetic material 22 is deposited over the external surface of substrate portion 12 and polymer 20 to lend hermeticity to the seal, thereby enclosing reservoirs 16 and effectively making each one a micro-hermetic chamber.

One challenge in placing the polymer into the reservoir opening is constraining the polymer to the intended location(s) of deposition. It may, for example, be undesirable for the polymer or polymer volatiles to interact with the reservoir contents. This may require the use of another barrier material (e.g., a barrier polymer) that can be in direct contact with the reservoir contents.

Figure 2:
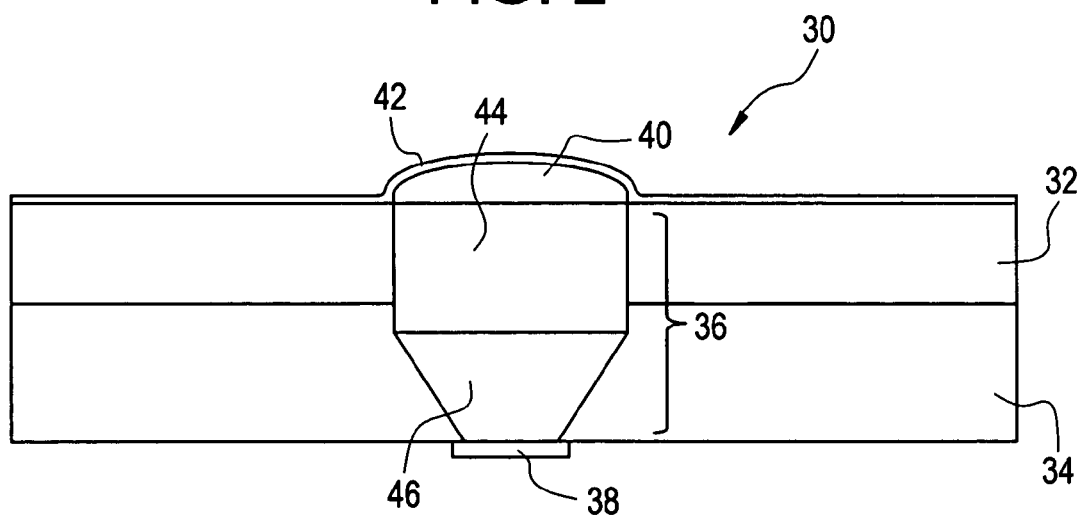
FIG. 2 is a cross-sectional view of a portion of another embodiment of a reservoir device sealed as described herein.

FIG. 2 shows a micro-reservoir device 30 that includes the use of a barrier layer, such as to thermally insulate the reservoir contents. The device 30 includes substrate portions 32 and 34, and reservoir 36 covered by reservoir cap 38. (The device typically would include an array of several identical such reservoirs, but for simplicity only one reservoir is shown.) Protective barrier material 44 (i.e., insulating layer) is shown located in direct contact with (on top of and next to) the reservoir contents 46, in reservoir 36. (Alternatively, the geometry of the substrate portions defining the reservoir can be modified to prevent direct contact.) The protective material 44 can be, for example, a biocompatible polymer or an inorganic substance, which would be loaded into the reservoir after the reservoir contents 46 are positioned in the reservoir 36. The device 30 further includes polymer 40 is deposited on protective material 17 forming a (temporary) seal of the end of reservoir 36. Then, hermetic material 42 is deposited over the external surface of substrate portion 32 and polymer 40 to hermetically seal reservoir 36.

Polymer volatiles can be minimized by, for example, vacuum baking thermoplastics and using thermosets that react to near completion. Rapidly curing a thermoset will also minimize volatiles created by the uncured thermoset vapor pressure.

In order for the coating for every individual reservoir to be hermetic, adjacent reservoirs cannot be bridged by a polymer pathway. Eliminating such pathways typically becomes difficult as the reservoir packing density in the substrate increases. For example, adjacent reservoirs may be separated by only a few hundred microns or less, so polymer placement and flow control becomes critical. It may be possible to pattern a biocompatible photodefinable polymer (such as polyimide) over the reservoir and remove it from the "streets" between reservoirs using a dry etch. It may also be possible to cure a thermoset in place with a pulse of heat as soon as it reaches the desired location during deposition. Similarly, a thermoplastic could be placed over the reservoir as a solid mass and heated until it flowed into the correct position and then actively or passively cooled. The reservoir geometry may also be modified to control the polymer wetting. For example, sharp edges created in the reservoir walls will cause a liquid polymer to preferentially wet the edge in order to reduce the polymer surface energy.

Figure 3A:
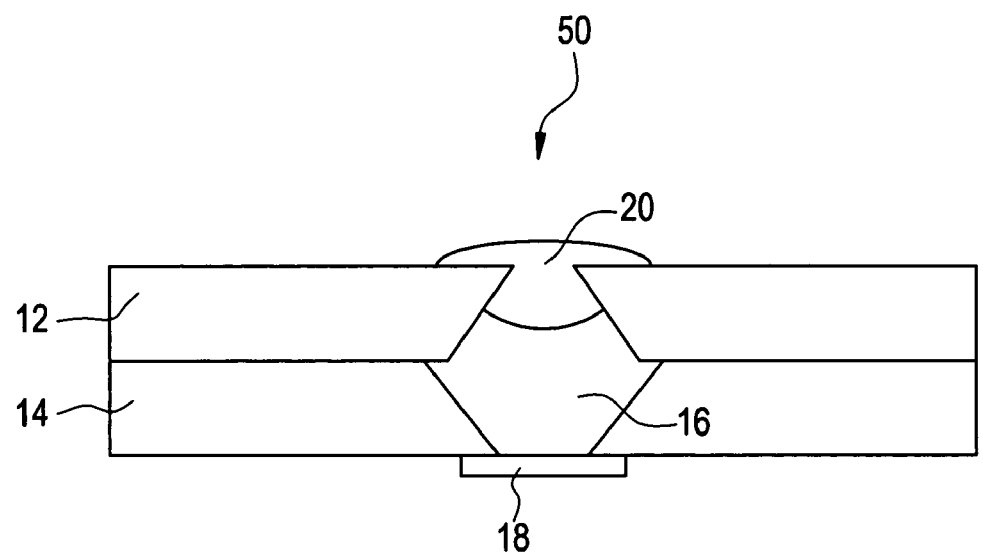
FIGS. 3A and 3B are cross-sectional views of two further embodiments of reservoir devices sealed as described herein, showing how reservoir geometry can be used to control wetting of the polymer at the reservoir opening.
Figure 3B:
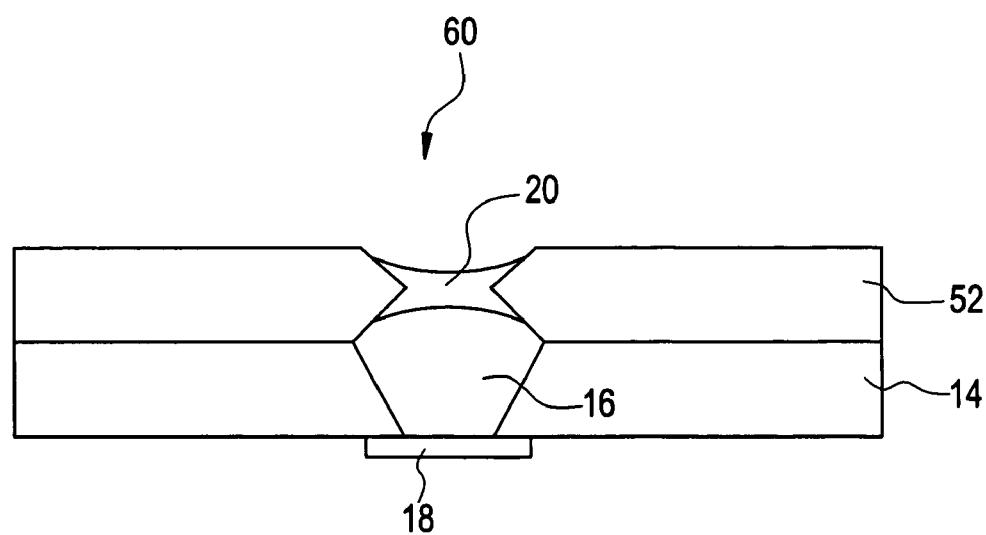

An example of how the reservoir geometry can be used to control wetting of the polymer is illustrated in FIGS. 3A and 3B. FIG. 3A shows micro-reservoir device 50 with substrate portions 12 and 14, a reservoir 16, and reservoir cap 18. The substrate portion 12 is shaped to define a reservoir where the upper portion tapers towards the opening of the reservoir, distal the reservoir cap. Polymer 20, deposited in the reservoir opening, forms a temporary seal of the reservoir opening. FIG. 3B shows micro-reservoir device 60, which like device 50, comprises with substrate portion 14, a reservoir 16, and reservoir cap 18. Device 60, however, includes substrate portion 52, which is shaped to define a reservoir that tapers towards the midpoint of the substrate portion, widening towards the opening, such that polymer 20, deposited in this reservoir opening, forms a temporary seal at the narrower region of the reservoir, as shown in FIG. 3B. The configuration in FIG. 3B has the advantage of exposing the interface between the polymer 20 and substrate 52 more directly to the deposition flux. Another advantage to device 60 compared to device 50 is that the polymer 20 tapers and thins as it approaches the transition to the substrate 52 walls. This thinning presents a less abrupt step for the barrier layer to be applied to.

In other embodiments of varying structural features or geometry, deposition of the polymer in a defined area is controlled by varying the shape or other characteristics of the substrate surface outside of the reservoir opening, beyond the sidewalls, i.e., on the streets between reservoir openings. For example, structures, such as trenches around each reservoir could be formed (e.g., by etching). In one method, the polymer is deposited into the reservoir and spreads along the area of the streets of the substrate until the polymer reaches the trench. Some of the polymer may enter the trench, but one would not deposit so much polymer into a single reservoir that it would flood (and overflow) the trench. The area of the streets of the substrate between neighboring trenches remain uncoated by the polymer, providing a clear area for contacting the hermetic seal material with the substrate. This enables a clean hermetic material-to-hermetic material interface (seal) to be made, avoiding any polymer bridges between neighboring reservoirs. The number, depth, shape, and spacing of the trenches can be varied as needed to achieve a suitable seal.

Figure 5A:
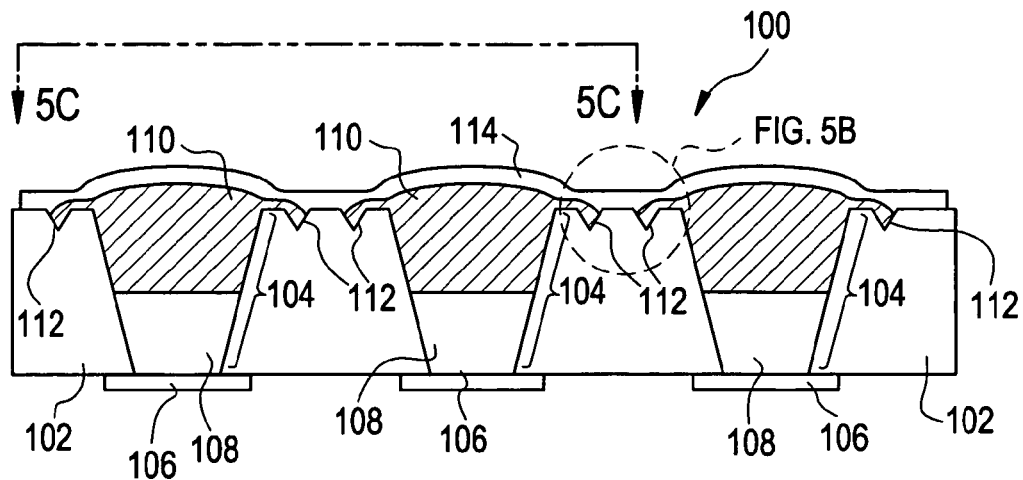
FIGS. 5A–C illustrate an embodiment of the sealing methods described herein where trenches are used to contain the polymer sealing material to a controlled area.
Figure 5B:
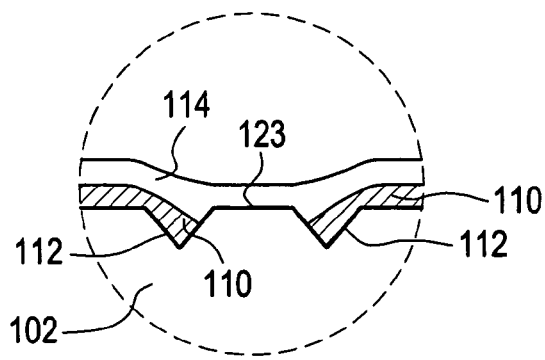
Figure 5C:
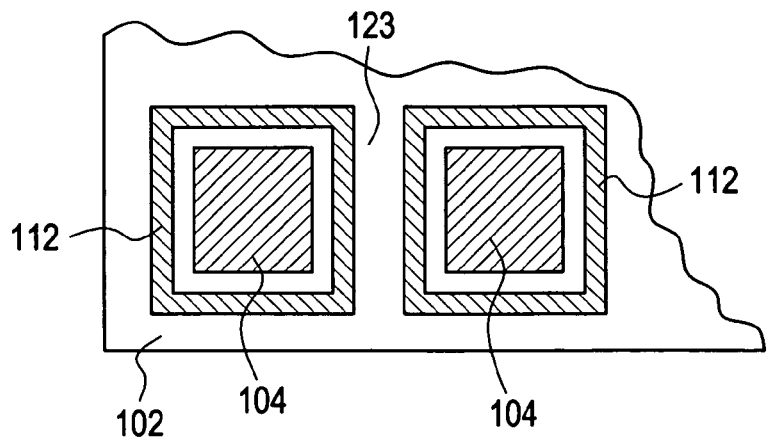

An example of this is shown in FIGS. 5A–C. FIG. 5A shows sealed micro-reservoir device 100 having substrate 102 with three reservoirs 104 containing reservoir contents 108. One end of the reservoirs are covered by reservoir caps 106. The reservoirs' openings distal the reservoir caps each are surrounded by trenches 112. For each reservoir, polymer 110 is deposited into the reservoir 104, filling the space in the reservoir unoccupied by the reservoir contents 108, and then flowing out of the reservoir and over an area of the substrate streets adjacent the reservoir opening, spreading until the polymer reaches the trench 112. A hermetic material 114 is deposited over the polymer 110 and contacts the polymer-free portions 123 of the substrate surface (i.e., streets) between neighboring trenches 112, as shown in FIG. 5A and FIG. 5B. FIG. 5C shows the device before the hermetic material is applied, and illustrates how the trenches 112 surround the reservoirs 104 in the substrate 102 and leave clean streets 123 between neighboring trenches.

In yet another embodiment, a separate impermeable component that the polymer wets that reduces the area to be sealed may also be incorporated in the well. The separate component functions as a solid plug in the reservoir opening and the polymer acts as to "caulk" the joint where the separate component and the edge of the reservoir opening interface. The separate component could be, for example, a biocompatible inorganic material such as a metal, glass, or ceramic that is itself not permeable to molecular species or an organic polymeric material. Ideally, the polymer would wet the surface of the separate component.

Figure 4A:
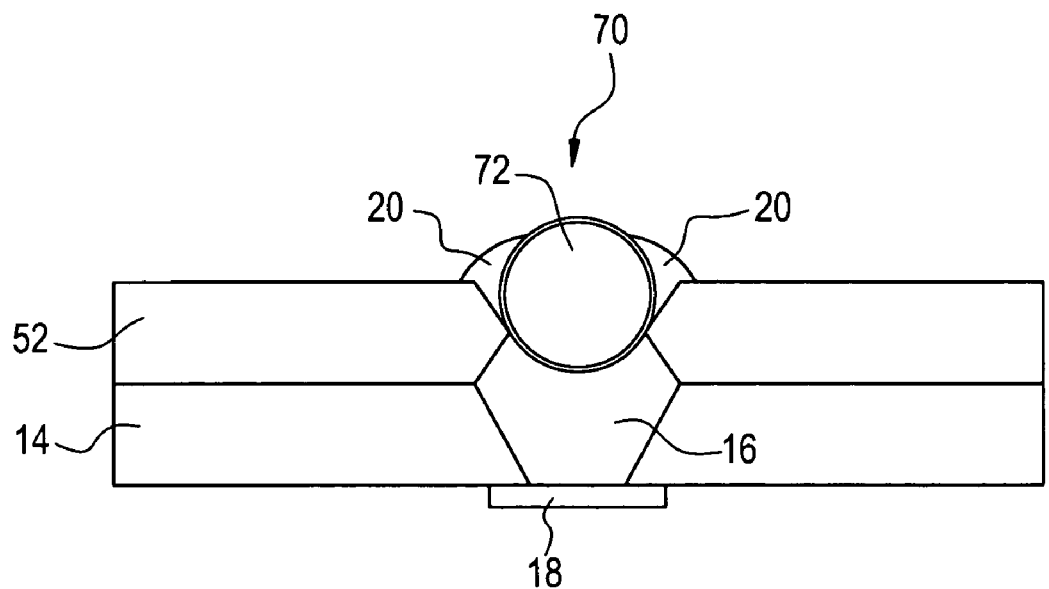
FIGS. 4A and 4B are cross-sectional views of another two embodiments of reservoir devices sealed as described herein, using a combination of a polymer sealant material and a plug component.
Figure 4B:
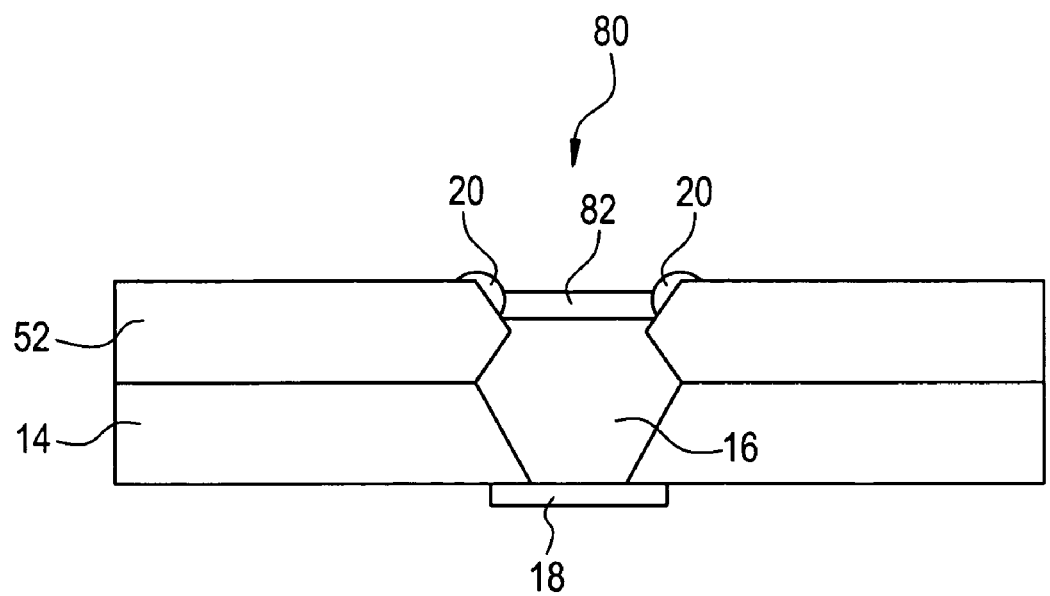

Two examples of this embodiment are illustrated in FIGS. 4A and 4B. FIG. 4A shows micro-reservoir device 70 with substrate portions 52 and 14, a reservoir 16, and reservoir cap 18. Substrate portion 52 is tapered towards the midpoint of the substrate portion. Plug component 72 is spherical, fitting into the socket shaped reservoir opening. Polymer 20 is deposited around the interface of plug component 72 and substrate portion 52. Together, the plug component 72 and polymer 20 cooperate to form a temporary seal of the reservoir 16. FIG. 4B shows similar device 80, wherein plug component 82 is in the shape of a flat mating piece that fits into the top portion of the reservoir. Polymer 20 is deposited around the interface of plug component 82 and substrate portion 52. The plug component 82 and polymer 20 cooperate to form a temporary seal of reservoir 16. In each case, the small space between the reservoir sidewall and the component 72 or 82 will cause capillary forces to restrict the flow of wetting polymers to the gap.

In other embodiments, the surface energy in specific locations around the reservoir may be controlled by depositing and patterning a chemical, to make use of surface tension effects in order to control the wetting of the polymer to specific locations on the substrate and thus control polymer flow.

In one embodiment, it may be desirable to modify the surface chemistry of the "streets" between the reservoirs to cause the polymer to wet the surface only in select areas. In other words, the polymer could be permitted to flow on the streets until it reached a region where the surface chemistry kept it from flowing any further. Such surface chemistry modifications could be made, for example, using hydrophilic or hydrophobic coatings, self-assembled monolayers, or photo-definable coatings.

In another aspect of the sealing methods, it is possible to deposit the polymer, such that pathways (or bridges) between adjacent reservoirs are allowed to be formed, but are then removed in a subsequent step following polymer deposition. In one embodiment, this is accomplished using photodefinable polymers. In another embodiment, a metal mask is deposited over the polymer and then dry etching (e.g., oxygen plasma etching) of the exposed regions is used to remove any polymer pathways between reservoirs. In still another embodiment, the polymer is physically polished to remove the polymer pathways. Polishing until a small amount of the top substrate is removed should ensure the removal of any polymer pathways. Fixed abrasives polishing pads or chemically compatible slurries may be used to remove the polymer. Polishing chemistry may be altered to enhance the selectivity between the polishing rates of the top substrate and the polymer. For example, a polymer solvent can be used in conjunction with a polishing pad to remove the polymer without polishing the top substrate. In this case, the top substrate would act as a polishing stop. In another embodiment, a laser may be used to ablate containments of the surface after the polymer has been applied. The laser can be controlled to only remove material from the sealing surfaces, or "streets".

The Polymeric Material

The polymeric material can be applied in a number of ways, depending for example on the type or form of the polymeric material. A variety of biocompatible polymers could be suitable for use as the polymeric material. In one embodiment, the polymer is a thermoplastic. Alternatively, the polymer is a thermoset. The selection of thermoplastic or thermoset governs how the polymer is applied, e.g., how fluidized, positioned, and then solidified in the selected location and form. Representative examples of suitable thermoplastics include polyvinyl alcohol, ethylene vinyl acetate copolymers, polyethylene, polyethylene terephthalate (e.g., MYLAR™), plasticized polyvinyl chloride, neoprene rubber, natural gum rubber, rubber hydrochloride (e.g., PLIOFILM™), polystyrene, polypropylene, polymethylacrylate, polyester/polyether copolymer, polypropylene/ethylene-propylene-diene monomer (EPDM), and other thermoplastic elastomers, (e.g., SANTOPRENE™). Representative examples of suitable thermoset polymers include class VI certified epoxies available from epoxy manufacturers such as Epotek's ND353 and 302M products, and Loctite M121HP epoxy, as well as polyurethanes and silicones.

In one embodiment, the thermoset is applied such that the reservoir is underfilled, providing a smooth transition between reservoir side walls and the polymeric material.

Another alternative is to use glass like structures such as sol-gel formation, which may or may not be sintered to close their structure. Silica-gel materials may also be used as a desiccant in the closing of a reservoir, preparing it for the hermetic layer.

The selected polymer must possess several characteristics in order to be suitable for use with this sealing technique. First, the polymer must interact/bond with the substrate strongly enough to remain in place during the deposition of the hermetic coating, which is generally performed in a reduced pressure environment. If the contents of the reservoir are at atmospheric pressure, the pressure difference across the polymer may act to dislodge it. Coupling agents or mechanical roughening may be required to increase the bond strength between substrate portion and polymer. Second, because changes in the polymer morphology during the hermetic material deposition process can disrupt the hermetic coating, a thermoplastic polymer typically should remain below the glass transition temperature during the hermetic material deposition processes to prevent undesirable polymer flow. The substrate portion and polymer can be cooled during deposition to prevent this problem; however, controlled cooling is needed so that thermal expansion (contraction) problems are avoided. Finally, the polymer may also have to act as a mass transfer barrier to prevent the reservoir environment from changing prior to the deposition of the hermetic seal. For instance, if the content of the reservoir is a liquid, the polymer must act as a moisture barrier to minimize evaporation until the hermetic material coating is deposited. The polymer also may be required to prevent environmental species (water, oxygen, etc.) from ingressing into the reservoir.

In one embodiment, the polymeric material comprises a biodegradable polymer. Examples include polyanhydrides, polylactic acid (PLA), polyglycolic acid (PGA), copolymers thereof (PLGA), and ethyl-vinyl acetate (EVA) polymers, where additional measures can be taken to have the material bind to the substrate and maintain the required insulating functionality (e.g., temperature stability). For example, it may be possible to put a monolayer coating on the substrate to help the polymeric material bind to the substrate.

In one embodiment, the polymeric material comprises a liquid crystal polymer film, e.g., a polyester-based liquid crystal polymer. In one embodiment, the liquid crystal polymer film or other polymeric material comprises one or more filler materials. Examples of filler materials include Au particles or $Al_2O_3$ particles. These fillers can drastically reduce the permeability of the temporary seal, can provide a surface with improved adhesion characteristics, and can alter the coefficient of thermal expansion of the temporary seal to provide an average composite coefficient of thermal expansion that is more closely matched to that of the substrate.

Dispensing the polymer into the reservoir typically poses several challenges. One challenge is the allowable thermal budget for polymer deposition. That is, the dispense temperature and/or the cure temperature of the polymer has to be low enough to prevent degradation of thermally sensitive contents in the reservoir, but high enough to remain solid during the hermetic coating deposition process. Thermoplastics can be dispensed in a molten state and allowed to solidify in place upon cooling. Thermosets can be dispensed in a liquid state and then heated to cure the thermoset in place. If the process temperature of the polymer is high relative the allowable thermal budget, infrared light or other direct means of isolating heat (e.g., finely directing it) to/in the polymer may be employed while the substrate (and drug) is cooled. Pulsed heating may also be employed to minimize the thermal load on the reservoir. For thermosets, the curing process may itself be significantly exothermic. In such cases, the curing process may need to be slowed to allow heat energy to dissipate through the substrate and minimize heating of the drug contents in the reservoir. Light curable thermosets may be used where the reservoir experiences minimal heating.

Polymer deposition may also be accomplished by delivering the polymer in a volatile solvent and allowing the solvent to evaporate. Finally, a thermally insulating material (i.e., a barrier layer) may be interposed between the reservoir contents and the temporary polymer seal to minimize heat conduction to the reservoir contents.

In one embodiment, the polymeric material comprises a desiccant material known in the art, so that the polymeric material can advantageously aid in removing any trace moisture from the reservoir.

The Hermetic Material

As it is generally known that polymers alone typically cannot form a hermetic seal, especially with the small geometries (or leak path lengths) present in MEMs devices, the present methods include the deposition of a hermetic material layer on top of the temporary seal. The hermetic sealing material preferably is adhered to the sealing surface (made of a hermetic material) circumscribing the reservoir opening.

A variety of hermetic sealing materials may be used. It preferably is substantially inert in the containment device's storage and operational environment. It preferably is a biocompatible metal or non-metal (e.g., ceramic). Representative examples of hermetic sealing materials include titanium, platinum, gold, stainless steels, aluminum, tin, gold-tin, indium, indium-tin, gold-silicon, polysilicon, silicon dioxide, silicon nitride, titanium nitride, and combinations thereof. In one embodiment, the material is one described in U.S. Patent Application Publication No. 2003/0080085 A1 to Greenberg, et al.

In one embodiment, the hermetic sealing material comprises a liquid crystal polymer known in the art. While not truly a hermetic material, it may for a particular application function as hermetic material with the addition of appropriate filler materials.

The surface of the polymer may be activated to increase the coating adhesion to the polymer. Techniques commonly used to activate the polymer surface include oxygen plasma cleaning and ion etching. Roughening the polymer surface prior to deposition may enhance the coating adhesion. This can be accomplished by ion etching, chemical etching or a physically abrasive technique. The surface of the polymer can also be chemically modified to increase adhesion. The substrate may be rotated or otherwise translated during the deposition process to increase the coverage of surfaces that are not normal to the deposition flux. Electro-plating or electroless plating are also possible, but less desirable because the plating solution could permeate the polymer with moisture or non-biocompatible chemicals.

The Barrier Layer

In one embodiment, the method may further include interposing an barrier layer between the reservoir contents and the polymeric material. Such a barrier material may serve as a diffusion barrier for heat (as described above) or mass or both, depending on the chemical sensitivity of the reservoir contents. Preferably, the barrier layer material is non-reactive with the polymeric material or with the reservoir contents.

The barrier layer may be, for example, a biocompatible polymer or an inorganic substance. In one embodiment, the barrier material comprises a wax. In another example, the barrier material comprises a polyethylene oxide. In yet another example, the barrier layer is a plug made of ceramic or a metal.

In one embodiment, the barrier layer is made by dispensing into the reservoir a liquid barrier layer precursor material and then reacting the precursor material to form the barrier layer. For example, the precursor could be one for yielding a synthetic polymer, a sol gel glass or ceramic, or a biopolymer. Examples of synthetic polymer include epoxies, silicones, and polyurethanes. Examples of sol gels include silica sol gel and titania sol gel. For instance, silica sol gel can be made by a condensation polymerization of alkoxysilanes (e.g., tetramethoxy silane). It can be an acid-catalyzed reaction, or it can be done at neutral pH using biological molecules (e.g., enzymes). In another embodiment, the precursor could be one for yielding a biopolymer. Examples include albumin glutaraldehyde and calcium alginate. Glutaraldehyde crosslinking is widely used, for example, in biosensor applications for enzyme immobilization. For example, a protein such as albumin in solution is provided and then glutaraldehyde is added, which reacts with amino groups on the proteins forming a gel. Alginate is another biopolymer, derived from seaweed, that is anionic. The sodium salt is soluble in water, but when sodium is exchanged for calcium the material crosslinks to form a gel.

In one embodiment, a barrier layer precursor material is dispensed into the reservoir and then is reacted to form the barrier layer. For example, the barrier layer can be selected from among synthetic polymers, sol gel glasses or ceramics, and biopolymers. In one embodiment, the synthetic polymer comprises an epoxy, a silicone, or a polyurethane. In another embodiment, the barrier layer comprises a silica sol gel or a titania sol gel. In yet another embodiment, the barrier layer comprises an alginate, albumin, glutaraldehyde, or combinations thereof.

In one embodiment, the barrier comprises multiple layers of materials. In one embodiment, multiple layers of a polymer are interposed with deposited hermetic coatings, adapting the teachings of U.S. Pat. No. 6,194,789 B1.

Deposition of the barrier layer can be accomplished using standard deposition techniques including physical vapor deposition or chemical vapor deposition. Other less common deposition techniques may also be employed such as jet vapor deposition, gas flow deposition, ion beam-assisted deposition, and any other technique that creates a contiguous hermetic coating.

The barrier layer may include a liquid crystal polymer film. In one embodiment, it includes a filler material to modify the hermeticity, coefficient of thermal expansion, adhesion characteristics, or other properties of the barrier layer.

The Containment Device

The hermetic sealing methods can be used to seal reservoirs in a variety of containment devices. In one embodiment, the reservoirs are part of an implantable drug delivery device, an implantable sensor device, or other medical device. Examples of such reservoir devices are described in U.S. Pat. No. 5,797,898, No. 6,551,838, No. 6,527,762, as well as in U.S. patent application publications No. 2002/0099359 and No. 2003/0010808, which are incorporated herein by reference.

In one embodiment, the device comprises a microchip chemical delivery device. In another embodiment, the device includes polymeric chips or devices composed of non-silicon based materials that might not be referred to as "microchips." In one embodiment, the device comprises an osmotic pump, for example, the DUROS™ osmotic pump technology (Alza Corporation) included in commercial devices such as VIADUR™ (Bayer Healthcare Pharmaceuticals and Alza Corporation).

In one embodiment, the containment device comprising the hermetically sealed reservoir is a subcomponent of another device. For example, it may be part of an implantable drug delivery device that further comprises a sensor indicative of a physiological condition of a patient, an electrode for providing electrical stimulation to the body of a patient, a pump, a catheter, or a combination thereof.

A. Substrate and Reservoirs

In one embodiment, the containment device comprises a body portion, i.e., a substrate, that includes one or more reservoirs for hermetically containing reservoir contents. That is, the substrate is the structural body (e.g., part of a device) in which the reservoirs are formed, e.g., it contains the etched, machined, or molded reservoirs. A reservoir is a well, a container, or a cavity. In a preferred embodiment, the device includes a plurality of the reservoirs located in discrete positions across at least one surface of the body portion.

Reservoirs can be fabricated in a structural body portion using any suitable fabrication technique known in the art. Representative fabrication techniques include MEMS fabrication processes or other micromachining processes, various drilling techniques (e.g., laser, mechanical, and ultrasonic drilling), and build-up techniques, such as LTCC (low temperature co-fired ceramics). The surface of the reservoir optionally can be treated or coated to alter one or more properties of the surface. Examples of such properties include hydrophilicity/hydrophobicity, wetting properties (surface energies, contact angles, etc.), surface roughness, electrical charge, release characteristics, and the like. MEMS methods, micromolding, micromachining, and microfabrication techniques known in the art can be used to fabricate the substrate/reservoirs from a variety of materials. Numerous other methods known in the art can also be used to form the reservoirs. See, for example, U.S. Pat. No. 6,123,861 and U.S. Patent Application Publication No. 2002/0107470.

In various embodiments, the body portion of the containment device comprises silicon, a metal, a ceramic, a polymer, or a combination thereof. Examples of suitable substrate materials include metals, ceramics, semiconductors, glasses, and degradable and non-degradable polymers. Preferably each reservoir is formed of hermetic materials (e.g., metals, silicon, glasses, ceramics) and is hermetically sealed by a reservoir cap. In a preferred embodiment, the substrate material is biocompatible and suitable for long-term implantation into a patient. In a preferred embodiment, the substrate is formed of one or more hermetic materials. The substrate, or portions thereof, may be coated, encapsulated, or otherwise contained in a hermetic biocompatible material (e.g., inert ceramics, titanium, and the like) before use. If the substrate material is not biocompatible, then it can be coated with, encapsulated, or otherwise contained in a biocompatible material, such as poly(ethylene glycol), polytetrafluoroethylene-like materials, diamond-like carbon, inert ceramics, titanium, and the like, before use. In one embodiment, the substrate is hermetic, that is impermeable (at least during the time of use of the reservoir device) to the molecules to be delivered and to surrounding gases or fluids (e.g., water, blood, electrolytes or other solutions). In another embodiment, the substrate is made of a material that degrades or dissolves over a defined period of time into biocompatible components. Examples of such materials include biocompatible polymers, such as poly(lactic acid)s, poly(glycolic acid)s, and poly(lactic-co-glycolic acid)s, as well as degradable poly(anhydride-co-imides).

The substrate can have a range of shapes or shaped surfaces. It can, for example, have a planar or curved surface, which for example could be shaped to conform to an attachment surface. In various embodiments, the substrate or the containment device is in the form of a chip, a circular or ovoid disk, a tube, a sphere, or a stent. The substrate can be flexible or rigid.

The substrate may consist of only one material, or may be a composite or multi-laminate material, that is, composed of several layers of the same or different substrate materials that are bonded together. Substrate portions (as in FIG. 1) can be, for example, silicon or another micromachined substrate or combination of micromachined substrates such as silicon and Pyrex glass, e.g., as described in U.S. patent application Ser. No. 09/665,303 or U.S. Pat. No. 6,527,762. In another embodiment, the substrate comprises multiple silicon wafers bonded together. In yet another embodiment, the substrate comprises a low-temperature co-fired ceramic (LTCC). In one embodiment, the body portion is the support for a microchip device. In one example, this substrate is formed of silicon.

Total substrate thickness and reservoir volume can be increased by bonding or attaching wafers or layers of substrate materials together. The device thickness may affect the volume of each reservoir and/or may affect the maximum number of reservoirs that can be incorporated onto a substrate. The size and number of substrates and reservoirs can be selected to accommodate the quantity and volume of reservoir contents needed for a particular application, manufacturing limitations, and/or total device size limitations to be suitable for implantation into a patient, preferably using minimally invasive procedures.

The substrate can have one, two, or preferably many, reservoirs. In various embodiments, tens, hundreds, or thousands of reservoirs are arrayed across the substrate. For instance, one embodiment of an implantable drug delivery device includes between 250 and 750 reservoirs, where each reservoir contains a single dose of a drug for release. In one sensing embodiment, the number of reservoirs in the device is determined by the operation life of the individual sensors. For example, a one-year implantable glucose monitoring device having individual sensors that remain functional for 30 days after exposure to the body would contain at least 12 reservoirs (assuming one sensor per reservoir). In another sensor embodiment, the distance between the sensor surface and the reservoir opening means is minimized, preferably only a few microns. In this case, the volume of the reservoir is primarily determined by the surface area of the sensor. For example, the electrodes of a typical enzymatic glucose sensor may occupy a space that is 400 µm by 800 µm.

In one embodiment, the reservoirs are microreservoirs. As used herein, the term "microreservoir" refers to a concave-shaped solid structure suitable for releasably containing a material, wherein the structure is of a size and shape suitable for filling with a microquantity of the material, which comprises a drug. In one embodiment, the microreservoir has a volume equal to or less than 500 µL (e.g., less than 250 µL, less than 100 µL, less than 50 µL, less than 25 µL, less than 10 µL, etc.) and greater than about 1 nL (e.g., greater than 5 nL, greater than 10 nL, greater than about 25 nL, greater than about 50 nL, greater than about 1 µL, etc.). The shape and dimensions of the microreservoir can be selected to maximize or minimize contact area between the drug material and the surrounding surface of the microreservoir.

As used herein, the term "microquantity" refers to small volumes between 1 nL and 10 µL. In one embodiment, the microquantity is between 1 nL and 1 µL. In another embodiment, the microquantity is between 10 nL and 500 nL.

In other embodiments, the reservoirs are larger than microreservoirs and can contain a quantity of drug formulation larger than a microquantity. For example, the volume of each reservoir can be greater than 10 µL (e.g., at least 20 µL, at least 50 µL, at least 100 µL, at least 250 µL, etc.) and less than 1,000 µL (e.g., less than 900 µL, less than 750 µL, less than 500 µL, less than 300 µL, etc.). These may be referred to as macro-reservoirs and macro-quantities, respectively. Unless explicitly indicated to be limited to either micro- or macro-scale volumes/quantities, the term "reservoir" is intended to include both.

In one embodiment, the device comprises a microchip chemical delivery device. In another embodiment, the device includes polymeric chips or devices composed of non-silicon based materials that might not be referred to as "microchips." In one embodiment, the device comprises an osmotic pump, for example, the DUROS™ osmotic pump technology (Alza Corporation) included in commercial devices such as VIADUR™ (Bayer Healthcare Pharmaceuticals and Alza Corporation).

B. Reservoir Contents

The reservoir contents is essentially any object or material that needs to be isolated (e.g., protected from) the environment outside of the reservoir until a selected point in time, when its release or exposure is desired. In various embodiments, the reservoir contents comprise (a quantity of) chemical molecules, a secondary device, or a combination thereof.

Proper functioning of certain reservoir contents, such as a catalyst or sensor, generally does not require release from the reservoir; rather their intended function, e.g., catalysis or sensing, occurs upon exposure of the reservoir contents to the environment outside of the reservoir after opening of the reservoir cap. Thus, the catalyst molecules or sensing component can be released or can remain immobilized within the open reservoir. Other reservoir contents such as drug molecules often may need to be released from the reservoir in order to pass from the device and be delivered to a site in vivo to exert a therapeutic effect on a patient. However, the drug molecules may be retained within the reservoirs for certain in vitro applications.

The environment of the reservoir contents may be modified to facilitate testing of individual reservoir hermeticity at a later time. In one embodiment, the item or material to be isolated is inserted into and isolated in the reservoir while in a gas rich environment, such as helium. The helium then can be used in a test, such as helium leak detection, to determine the leak rates of individual reservoir seals. In another embodiment, the contents of a reservoir would be dispensed and sealed in vacuum, such that the difference in pressure could be used to determine the quality of the hermetic seal. For example, one may use observed deflection of the reservoir cap to determine if a particular reservoir is holding vacuum and is hermetic.

Chemical Molecules

The reservoir contents can include essentially any natural or synthetic, organic or inorganic molecules or mixtures thereof. The molecules may be in essentially any form, such as a pure solid or liquid, a gel or hydrogel, a solution, an emulsion, a slurry, or a suspension. The molecules of interest may be mixed with other materials to control or enhance the rate and/or time of release from an opened reservoir. In various embodiments, the molecules may be in the form of solid mixtures, including amorphous and crystalline mixed powders, monolithic solid mixtures, lyophilized powders, and solid interpenetrating networks. In other embodiments, the molecules are in liquid-comprising forms, such as solutions, emulsions, colloidal suspensions, slurries, or gel mixtures such as hydrogels.

In a preferred embodiment, the reservoir contents comprise a drug formulation. The drug formulation is a composition that comprises a drug. As used herein, the term "drug" includes any therapeutic or prophylactic agent (e.g., an active pharmaceutical ingredient or API). In one embodiment, the drug is provided in a solid form, particularly for purposes of maintaining or extending the stability of the drug over a commercially and medically useful time, e.g., during storage in a drug delivery device until the drug needs to be administered. The solid drug matrix may be in pure form or in the form of solid particles of another material in which the drug is contained, suspended, or dispersed. In one embodiment, the drug is formulated with an excipient material that is useful for accelerating release, e.g., a water-swellable material that can aid in pushing the drug out of the reservoir and through any tissue capsule over the reservoir.

The drug can comprise small molecules, large (i.e., macro-) molecules, or a combination thereof. In one embodiment, the large molecule drug is a protein or a peptide. In various other embodiments, the drug can be selected from amino acids, vaccines, antiviral agents, gene delivery vectors, interleukin inhibitors, immunomodulators, neurotropic factors, neuroprotective agents, antineoplastic agents, chemotherapeutic agents, polysaccharides, anti-coagulants (e.g., LMWH, pentasaccharides), antibiotics (e.g., immunosuppressants), analgesic agents, and vitamins. In one embodiment, the drug is a protein. Examples of suitable types of proteins include, glycoproteins, enzymes (e.g., proteolytic enzymes), hormones or other analogs (e.g., LHRH, steroids, corticosteroids, growth factors), antibodies (e.g., anti-VEGF antibodies, tumor necrosis factor inhibitors), cytokines (e.g., α-, β-, or γ-interferons), interleukins (e.g., IL-2, IL-10), and diabetes/obesity-related therapeutics (e.g., insulin, exenatide, PYY, GLP-1 and its analogs). In one embodiment, the drug is a gonadotropin-releasing (LHRH) hormone analog, such as leuprolide. In another exemplary embodiment, the drug comprises parathyroid hormone, such as a human parathyroid hormone or its analogs, e.g., HPTH(1-84) or hPTH(1-34). In a further embodiment, the drug is selected from nucleosides, nucleotides, and analogs and conjugates thereof. In yet another embodiment, the drug comprises a peptide with natriuretic activity, such as atrial natriuretic peptide (ANP), B-type (or brain) natriuretic peptide (BNP), C-type natriuretic peptide (CNP), or dendroaspis natriuretic peptide (DNP). In still another embodiment, the drug is selected from diuretics, vasodilators, inotropic agents, anti-arrhythmic agents, Ca$^+$ channel blocking agents, anti-adrenergics/sympatholytics, and renin angiotensin system antagonists. In one embodiment, the drug is a VEGF inhibitor, VEGF antibody, VEGF antibody fragment, or another anti-angiogenic agent. Examples include an aptamer, such as MACUGEN™ (Pfizer/Eyetech) (pegaptanib sodium)) or LUCENTIS™ (Genetech/Novartis) (rhuFab VEGF, or ranibizumab), which could be used in the prevention of choroidal neovascularization (useful in the treatment of age-related macular degeneration or diabetic retinopathy). In yet a further embodiment, the drug is a prostaglandin, a prostacyclin, or another drug effective in the treatment of peripheral vascular disease.

In still another embodiment, the drug is an angiogenic agent, such as VEGF. In a further embodiment, the drug is an anti-inflammatory, such as dexamethasone. In one embodiment, a device includes both angiogenic agents and anti-inflammatory agents.

The reservoirs in one device can include a single drug or a combination of two or more drugs, and/or two or more transport enhancers, and can further include one or more pharmaceutically acceptable carriers. Two or more transport enhancers, angiogenic agents, anti-inflammatory agents, or combinations thereof, can be stored together and released from the same one or more reservoirs or they can each be stored in and released from different reservoirs.

For in vitro applications, the chemical molecules can be any of a wide range of molecules where the controlled release of a small (milligram to nanogram) amount of one or more molecules is required, for example, in the fields of analytic chemistry or medical diagnostics. Molecules can be effective as pH buffering agents, diagnostic reagents, and reagents in complex reactions such as the polymerase chain reaction or other nucleic acid amplification procedures. In various other embodiments, the molecules to be released are fragrances or scents, dyes or other coloring agents, sweeteners or other concentrated flavoring agents, or a variety of other compounds. In yet other embodiments, the reservoirs contain immobilized molecules. Examples include any chemical species which can be involved in a reaction, including reagents, catalysts (e.g., enzymes, metals, and zeolites), proteins, nucleic acids, polysaccharides, cells, and polymers, as well as organic or inorganic molecules which can function as a diagnostic agent.

The drug or other molecules for release can be dispersed in a matrix material, to control the rate of release. This matrix material can be a "release system," as described in U.S. Pat. No. 5,797,898, the degradation, dissolution, or diffusion properties of which can provide a method for controlling the release rate of the chemical molecules.

Particularly for drugs, the release system may include one or more pharmaceutical excipients. The release system may provide a temporally modulated release profile (e.g., pulsatile release) when time variation in plasma levels is desired or a more continuous or consistent release profile when a constant plasma level as needed to enhance a therapeutic effect, for example. Pulsatile release can be achieved from an individual reservoir, from a plurality of reservoirs, or a combination thereof. For example, where each reservoir provides only a single pulse, multiple pulses (i.e. pulsatile release) are achieved by temporally staggering the single pulse release from each of several reservoirs. Alternatively, multiple pulses can be achieved from a single reservoir by incorporating several layers of a release system and other materials into a single reservoir. Continuous release can be achieved by incorporating a release system that degrades, dissolves, or allows diffusion of molecules through it over an extended period. In addition, continuous release can be approximated by releasing several pulses of molecules in rapid succession ("digital" release). The active release systems described herein can be used alone or on combination with passive release systems, for example, as described in U.S. Pat. No. 5,797,898. For example, the reservoir cap can be removed by active means to expose a passive release system, or a given substrate can include both passive and active release reservoirs.

In one embodiment, the drug formulation within a reservoir comprises layers of drug and non-drug material. After the active release mechanism has exposed the reservoir contents, the multiple layers provide multiple pulses of drug release due to intervening layers of non-drug.

Secondary Devices

As used herein, unless explicitly indicated otherwise, the term "secondary device" includes any device or a component thereof that can be located in a reservoir. In one embodiment, the secondary device is a sensor or sensing component thereof. As used herein, a "sensing component" includes a component utilized in measuring or analyzing the presence, absence, or change in a chemical or ionic species, energy, or one or more physical properties (e.g., pH, pressure) at a site. Types of sensors include biosensors, chemical sensors, physical sensors, or optical sensors. Secondary devices are further described in U.S. Pat. No. 6,551,838. In one embodiment, the sensor is a pressure sensor. See, e.g., U.S. Pat. No. 6,221,024, and No. 6,237,398, and U.S. Patent Application Publication No. 2004/0073137. Examples of sensing components include components utilized in measuring or analyzing the presence, absence, or change in a drug, chemical, or ionic species, energy (or light), or one or more physical properties (e.g., pH, pressure) at a site.

In one embodiment, a device is provided for implantation in a patient (e.g., a human or other mammal) and the reservoir contents comprises at least one sensor indicative of a physiological condition in the patient. For example, the sensor could monitor the concentration of glucose, urea, calcium, or a hormone present in the blood, plasma, interstitial fluid, vitreous humor, or other bodily fluid of the patient.

Several options exist for receiving and analyzing data obtained with secondary devices located within the primary device, which can be a microchip device or another device. Devices may be controlled by local microprocessors or remote control. Biosensor information may provide input to the controller to determine the time and type of activation automatically, with human intervention, or a combination thereof. For example, the operation of the device can be controlled by an on-board (i.e., within the package) microprocessor. The output signal from the device, after conditioning by suitable circuitry if needed, will be acquired by the microprocessor. After analysis and processing, the output signal can be stored in a writeable computer memory chip, and/or can be sent (e.g., wirelessly) to a remote location away from the microchip. Power can be supplied to the microchip system locally by a battery or remotely by wireless transmission. See, e.g., U.S. Patent Application Publication No. 2002/0072784.

In one embodiment, a device is provided having reservoir contents that include drug molecules for release and a sensor/sensing component. For example, the sensor or sensing component can be located in a reservoir or can be attached to the device substrate. The sensor can operably communicate with the device, e.g., through a microprocessor, to control or modify the drug release variables, including dosage amount and frequency, time of release, effective rate of release, selection of drug or drug combination, and the like. The sensor or sensing component detects (or not) the species or property at the site of in vivo implantation and further may relay a signal to the microprocessor used for controlling release from the device. Such a signal could provide feedback on and/or finely control the release of a drug. In another embodiment, the device includes one or more biosensors (which may be sealed in reservoirs until needed for use) that are capable of detecting and/or measuring signals within the body of a patient.

In one variation, an implantable medical device includes reservoirs comprising sensor, sealed as described herein, and a signal from the sensor is transmitted (by any number of means, including hardwire or telemetry) to a separate drug delivery device, which could be a wearable (i.e., external) or internal pump, the signal being used in the control of the dosing of the drug.

As used herein, the term "biosensor" includes sensing devices that transduce the chemical potential of an analyte of interest into an electrical signal, as well as electrodes that measure electrical signals directly or indirectly (e.g., by converting a mechanical or thermal energy into an electrical signal). For example, the biosensor may measure intrinsic electrical signals (EKG, EEG, or other neural signals), pressure, temperature, pH, or mechanical loads on tissue structures at various in vivo locations. The electrical signal from the biosensor can then be measured, for example by a microprocessor/controller, which then can transmit the information to a remote controller, another local controller, or both. For example, the system can be used to relay or record information on the patient's vital signs or the implant environment, such as drug concentration.

In one embodiment, the device contains one or more sensors for use in glucose monitoring and insulin control. Information from the sensor could be used to actively control insulin release from the same device or from a separate insulin delivery device (e.g., a conventional insulin pump, either an externally worn version or an implanted version). Other embodiments could sense other analytes and delivery other types of drugs in a similar fashion.

C. Controlled Release/Exposure Mechanisms

The containment device preferably includes reservoir control means for opening the hermetically sealed reservoirs at a select time following sealing of the reservoirs as described herein. The control means comprises the structural component(s) for controlling the time at which release or exposure of the reservoir contents is initiated. In a preferred embodiment, the reservoir control means includes reservoir caps and the hardware, electrical components, and software needed to control and deliver electric energy from a power source to selected reservoir(s) for actuation, e.g., reservoir opening. In one embodiment, the hermetically sealed reservoir is closed at one surface by a reservoir cap operable for controlled opening of the reservoir.

The control means can take a variety of forms. In one embodiment, each reservoir has an opening covered by a reservoir cap that can be selectively ruptured (e.g., disintegrated) to initiate release of the drug from the reservoir. For example, the reservoir cap can comprise a metal film that is disintegrated by electrothermal ablation as described in U.S. Patent Application Publication No. 2004/0121486 A1. Other reservoir opening and release control methods are described in U.S. Pat. No. 5,797,898, No. 6,527,762, and No. 6,491,666, U.S. Patent Application Publication Nos. 2002/0107470 A1, 2002/0072784 A1, 2002/0138067 A1, 2002/0151776 A1, 2002/0099359 A1, 2002/0187260 A1, and 2003/0010808 A1; PCT WO 2004/022033 A2; PCT WO 2004/026281; and U.S. Pat. Nos. 5,797,898; 6,123,861; and 6,527,762, all of which are incorporated by reference herein.

For example, the reservoir cap could include any material that can be disintegrated or permeabilized in response to an applied stimulus (e.g., electric field or current, magnetic field, change in pH, or by thermal, chemical, electrochemical, or mechanical means). In one embodiment, the reservoir cap is a thin metal membrane and is impermeable to the surrounding environment (e.g., body fluids or another chloride containing solution), and which is disintegrated by electrochemical dissolution via the application of electrical potential. In another embodiment, a controlled heating of the reservoir cap causes it to rupture. In yet another embodiment, an electro-resistive ablation technique is used to disintegrate/rupture the reservoir cap by selectively passing electrical current through a conductive reservoir cap as taught in U.S. Patent Application Publication No. 2004/0121486 A1.

As used herein, the term "reservoir cap" includes a membrane or other structure suitable for separating the contents of a reservoir from the environment outside of the reservoir. It generally is self-supporting across the reservoir opening, although caps having additional structures to provide mechanical support to the cap can be fabricated. See, e.g., U.S. Patent Application Publication Nos. 2002/0183721 A1. Reservoir caps can be made using MEMS or other techniques and designed/fabricated to open to the external environment upon activation by any of a number of methods, including those taught in U.S. Pat. No. 6,527,762, U.S. Pat. No. 5,797,898, and U.S. Patent Application Publication No. 2004/0121486 A1.

Selectively removing the reservoir cap or making it permeable will then "expose" the contents of the reservoir to the environment (or selected components thereof) surrounding the reservoir. In preferred embodiments, the reservoir cap is selectively disintegrated. As used herein, the term "disintegrate" includes degrading, dissolving, rupturing, fracturing or some other form of mechanical failure, as well as a loss of structural integrity due to a chemical reaction (e.g., electrochemical degradation) or phase change (e.g., melting) in response to a change in temperature, unless a specific one of these mechanisms is indicated. In one specific embodiment, the "disintegration" is by an electrochemical activation technique, such as described in U.S. Pat. No. 5,797,898. In another specific embodiment, the "disintegration" is by an electro-thermal ablation technique, as described in U.S. Patent Application Publication No. 2004/0121486 A1.

In one embodiment, the reservoir cap is a thin metal film and is impermeable to the surrounding environment (e.g., body fluids or another chloride containing solution). In one variation, a particular electric potential is applied to the metal reservoir cap, which is then oxidized and disintegrated by an electrochemical reaction, to release the drug from the reservoir. Examples of suitable reservoir cap materials include gold, silver, copper, and zinc.

In another variation, the reservoir cap is heated (e.g., using resistive heating) to cause the reservoir cap to melt and be displaced from the reservoir to open it. This latter variation could be used, for example, with reservoir caps formed of a metal or a non-metal material, e.g., a polymer. In yet another variation, the reservoir cap is formed of a polymer or other material that undergoes a temperaturedependent change in permeability such that upon heating to a pre-selected temperature, the reservoir is rendered permeable to the drug and bodily fluids to permit the drug to be released from the reservoir through the reservoir cap.

In still another embodiment, the reservoir cap is formed of a conductive material, such as a metal film, through which an electrical current can be passed to electrothermally ablate it, as described in U.S. Patent Application Publication No. 2004/0121486 A1. Representative examples of suitable reservoir cap materials include gold, copper, aluminum, silver, platinum, titanium, palladium, various alloys (e.g., Au—Si, Au—Ge, Pt—Ir, Ni—Ti, Pt—Si, SS 304, SS 316), and silicon doped with an impurity to increase electrical conductivity, as known in the art. In one embodiment, the reservoir cap is in the form of a thin metal film. In one embodiment, the reservoir cap is part of a multiple layer structure, for example, the reservoir cap can be made of multiple metal layers, such as a multi-layer/laminate structure of platinum/titanium/platinum. The reservoir cap is operably (i.e., electrically) connected to an electrical input lead and to an electrical output lead, to facilitate flow of an electrical current through the reservoir cap. When an effective amount of an electrical current is applied through the leads and reservoir cap, the temperature of the reservoir cap is locally increased due to resistive heating, and the heat generated within the reservoir cap increases the temperature sufficiently to cause the reservoir cap to be electrothermally ablated and ruptured.

In passive release devices, the reservoir cap is formed from a material or mixture of materials that degrade, dissolve, or disintegrate over time, or that do not degrade, dissolve, or disintegrate, but are permeable or become permeable to molecules or energy. Representative examples of reservoir cap materials include polymeric materials, and non-polymeric materials such as porous forms of metals, semiconductors, and ceramics. Passive semiconductor reservoir cap materials include nanoporous or microporous silicon membranes.

Characteristics can be different for each reservoir cap to provide different times of release of drug formulation. For example, any combination of polymer, degree of crosslinking, or polymer thickness can be modified to obtain a specific release time or rate.

Any combination of passive and/or active release reservoir cap can be present in a single containment device. For example, the reservoir cap can be removed by electrothermal ablation to expose a passive release system that only begins its passive release after the reservoir cap has been actively removed. Alternatively, a given device can include both passive and active release reservoirs.

Using Devices with Hermetically Sealed Reservoirs

The hermetically-sealed devices described herein can be used in a wide variety of applications. Preferred applications include the controlled delivery of one or more drugs, biosensing, or a combination thereof.

In a preferred embodiment, the sealed reservoir device is part of an implantable medical device. The implantable medical device can take a wide variety of forms and be used in a variety of therapeutic and/or diagnostic applications. Examples include implantable controlled drug delivery devices, drug pumps (such as an implantable osmotic or mechanical pump), drug-eluting stents, and combinations thereof.

In one embodiment, the device includes hermetically-sealed reservoirs containing a drug formulation. For example, the device is implanted into a patient (such as a human or other vertebrate animal) using standard surgical or minimally-invasive implantation techniques, and then the reservoirs are opened on a schedule determined by the type of drug therapy prescribed by the physician.

In another embodiment, the device includes (i) active release reservoirs containing sensors.

In one embodiment, the hermetic sealing methods are used to hermetically seal sensors in a device until exposure to the environment is desired. The environment could be in vitro or in vivo, depending upon the particular application and device. In one embodiment, the sensor is a biosensor, and the reservoirs are opened as needed (depending, for example, upon fouling of the sensor) or as dictated by a predetermined schedule. In one embodiment, the sealed reservoirs contain pressure sensors.

In other embodiments, the hermetically sealed reservoirs described herein are incorporated into a variety of other devices. For example, the hermetically sealed reservoirs could be integrated into other types and designs of implantable medical devices, such as the catheters and electrodes described in U.S. Patent Application Publication No. 2002/0111601. In another example, it could be incorporated into another medical device, in which the present devices and systems release drug into a carrier fluid that then flows to a desired site of administration, as illustrated for example in U.S. Pat. No. 6,491,666. The hermetically sealed reservoirs also could be incorporated into a drug pump, a stent, or an inhaler or other pulmonary drug delivery device.

The devices have numerous in vivo, in vitro, and commercial diagnostic applications. The devices are capable of delivering precisely metered quantities of molecules and thus are useful for in vitro applications, such as analytical chemistry and medical diagnostics, as well as biological applications such as the delivery of factors to cell cultures. In still other non-medical applications, the devices are used to control release of fragrances, dyes, or other useful chemicals.

Methods of using and operating the devices are further described in U.S. Pat. Nos. 5,797,898; 6,527,762; 6,491,666; and 6,551,838, and U.S. Patent Application Publications 2002/0183721, 2003/0100865, 2002/0099359, 2004/0082937, 2004/0127942, 2004/0121486, 2004/0106914, and 2004/0106953, all of which are incorporated by reference herein.

Publications cited herein are incorporated by reference. Modifications and variations of the methods and devices described herein will be obvious to those skilled in the art from the foregoing detailed description. Such modifications and variations are intended to come within the scope of the appended claims.

We claim:

1. A method for hermetically sealing an opening in a reservoir of a containment device comprising:

applying a polymeric material to an opening in a reservoir of a containment device, the reservoir comprising reservoir contents to be hermetically isolated within the reservoir, the applied polymeric material closing off the opening and forming a temporary seal, wherein the reservoir is closed, at an end distal the opening in need of sealing, by a reservoir cap which can be selectively disintegrated or permeabilized to expose or release the reservoir contents; and adhering a hermetic sealing material onto the polymeric material to hermetically seal the opening.

2. The method of claim 1, wherein the reservoir is defined in a substrate which has a sealing surface circumscribing the opening of the reservoir.

3. The method of claim 2, wherein the substrate is formed of one or more hermetic materials.

4. The method of claim 2, wherein the sealing surface comprises one or more structures confining the location of the applied polymer.

5. The method of claim 4, wherein the one or more structures comprise a trench surrounding the reservoir.

6. The method of claim 2, wherein the hermetic sealing material is further adhered to the sealing surface at least in an area circumscribing the opening.

7. The method of claim 1, wherein the reservoir contents comprise a drug.

8. The method of claim 1, wherein the reservoir contents comprise a sensor.

9. The method of claim 1, wherein the polymeric material comprises a thermoplastic.

10. The method of claim 9, wherein the thermoplastic is applied to the opening in a molten state and then is cooled to solidify and form the temporary seal.

11. The method of claim 9 wherein the polymeric material comprises a filler material to modify the hermeticity and coefficient of thermal expansion characteristics of the temporary seal.

12. The method of claim 9, wherein the polymeric material comprises a desiccant.

13. The method of claim 1, wherein the polymeric material comprises a thermoset.

14. The method of claim 13, wherein the thermoset is applied to the opening in a liquid state and then is cured to solidify and form the temporary seal.

15. The method of claim 14, wherein the thermoset is cured by heating.

16. The method of claim 15, wherein heat is applied to the thermoset in a pulsed manner.

17. The method of claim 15, wherein the containment device or a portion thereof is cooled while the thermoset is being heated.

18. The method of claim 15, further comprising interposing a barrier layer between the reservoir contents and the polymeric material.

19. The method of claim 18, wherein a barrier layer precursor material is dispensed into the reservoir and then is reacted to form the barrier layer.

20. The method of claim 18, wherein the barrier layer is selected from the group consisting of synthetic polymers, sol gel glasses, sol ceramics, biopolymers, and combinations thereof.

21. The method of claim 20, wherein the synthetic polymer comprises an epoxy, a silicone, or a polyurethane.

22. The method of claim 20, wherein the barrier layer comprises a silica sol gel or a titania sol gel.

23. The method of claim 20, wherein the barrier layer comprises an alginate, albumin, glutaraldehyde, or a combination thereof.

24. The method of claim 14, wherein the thermoset is cured by light activation.

25. The method of claim 14, wherein the thermoset cures at ambient temperature after two or more hours.

26. The method of claim 14, wherein the thermoset is applied such that the reservoir is underfilled.

27. The method of claim 1, wherein the polymeric material comprises a photodefinable polymer.

28. The method of claim 1, wherein the polymeric material is applied to the opening in solution with a volatile solvent and ten the volatile solvent is evaporated to solidify the polymeric material and form the temporary seal.

29. The method of claim 1, wherein the polymeric material comprises a polyester-based liquid crystal polymer material.

30. The method of claim 1, further comprising placing a solid secondary component into the opening before or after the polymeric material is applied to the opening but before the hermetic sealing material is adhered.

31. The method of claim 1, wherein the reservoir is a micro-reservoir.

32. The method of claim 31, wherein the containment device comprises an array of two or more of micro-reservoirs, and the method further comprises sealing the two or more micro-reservoirs.

33. The method of claim 1, wherein the hermetic sealing material is selected from the group consisting of titanium, platinum, gold, stainless steels, aluminum, and combinations thereof.

34. The method of claim 1, wherein the hermetic sealing material is selected from the group consisting of tin, gold-tin, indium, indium-tin, gold-silicon, polysilicon, and combinations thereof.

35. The method of claim 1, wherein the hermetic sealing material is selected from the group consisting of silicon dioxide, silicon nitride, titanium nitride, and combinations thereof.

36. The method of claim 1, wherein the hermetic sealing material comprises a liquid crystal polymer.

37. A method for hermetically sealing a plurality of openings of reservoirs in a containment device comprising:
    providing a device which comprises a substrate in which a plurality of reservoirs are defined, the substrate having a sealing surface circumscribing the openings of the reservoirs;
    applying a polymeric material to the openings to close off the openings and form a temporary seal; and
    adhering a hermetic sealing material onto the polymeric material and onto the sealing surface to hermetically seal the openings.

38. The method of claim 37, further comprising, before applying the polymeric material, loading the reservoirs with reservoir contents, which are selected from the group consisting of drugs, sensors, and combinations thereof, wherein the method hermetically isolates the reservoir contents within the reservoir.

39. The method of claim 37, wherein one or more polymer pathways between said two or more reservoirs are formed by the application of the polymeric material and the polymer pathways are removed before the hermetic sealing material is adhered over the temporary seals.

40. The method of claim 39, wherein the polymer pathways are removed by dry etching, polishing, or laser ablation.

41. The method of claim 39, wherein a wetting control means is used to manipulate surface tension effects to limit the wetting of the polymer to specific locations on the surface of the substrate.

42. The method of claim 41, wherein the wetting control means comprises depositing and patterning a wetting control agent on the surface of the substrate before application of the polymeric material.

43. The method of claim 37, wherein the reservoirs are micro-reservoirs.

* * * * *

UNITED STATES PATENT AND TRADEMARK OFFICE
CERTIFICATE OF CORRECTION

PATENT NO.        : 7,114,312 B2             Page 1 of 1
APPLICATION NO.   : 10/894265
DATED             : October 3, 2006
INVENTOR(S)       : Coppeta et al.

It is certified that error appears in the above-identified patent and that said Letters Patent is hereby corrected as shown below:

On the Title Page under Item [56] "References Cited" the following additional references should appear in the list of "U.S. PATENT DOCUMENTS":

| | | |
|---|---|---|
| --5,493,177 | 2/1996 | Muller et al. |
| 6,429,511 B2 | 8/2002 | Ruby et al. |
| 6,853,067 B1 | 2/2005 | Cohn et al. |
| 6,872,902 B2 | 3/2005 | Cohn et al.-- |

On the Title Page under Item [56] "References Cited" the following additional references should appear in the list of "FOREIGN PATENT DOCUMENTS":

| | | | | |
|---|---|---|---|---|
| --WO | 2004/025727 A1 | 3/2004 | Niklaus et al. |
| EP | 0606725 A1 | 7/1994 | Blonder-- |

Signed and Sealed this

Fourteenth Day of August, 2007

JON W. DUDAS
*Director of the United States Patent and Trademark Office*